US005514690A

United States Patent [19]
Atwal et al.

[11] Patent Number: 5,514,690
[45] Date of Patent: May 7, 1996

[54] AMINOCARBONYL (THIOCARBONYL) AND CYANOGUANIDINE DERIVATIVES OF QUINOLINE AND INDOLINE

[75] Inventors: Karnail S. Atwal, Newtown, Pa.; Francis N. Ferrara, Martinsville, N.J.

[73] Assignee: E. R. Squibb & Sons, Inc., Princeton, N.J.

[21] Appl. No.: 111,239

[22] Filed: Aug. 24, 1993

Related U.S. Application Data

[63] Continuation-in-part of Ser. No. 977,340, Nov. 17, 1992, abandoned.
[51] Int. Cl.$^6$ .......................... A61K 31/47; A61K 31/44; C07D 215/58; C07D 401/00
[52] U.S. Cl. .......................... 514/311; 514/313; 514/339; 514/415; 546/152; 546/169; 546/171; 546/273; 548/469
[58] Field of Search ...................................... 546/152, 169, 546/171, 273; 548/469; 514/313, 311, 339, 415

[56] References Cited

U.S. PATENT DOCUMENTS

| 3,872,119 | 3/1975 | Kathawala | 548/491 |
|---|---|---|---|
| 3,953,506 | 4/1976 | Spicer et al. | 71/90 |
| 4,428,881 | 1/1984 | Hedrich et al. | 548/491 |
| 5,140,031 | 8/1992 | Atwal et al. | 514/302 |

FOREIGN PATENT DOCUMENTS

| 205292 | 12/1986 | European Pat. Off. . |
|---|---|---|
| 214818 | 3/1987 | European Pat. Off. . |
| 0247266 | 12/1987 | European Pat. Off. . |
| 274821 | 7/1988 | European Pat. Off. . |
| 0287196 | 10/1988 | European Pat. Off. . |
| 344747 | 12/1989 | European Pat. Off. . |
| 350805 | 1/1990 | European Pat. Off. . |
| 389861 | 3/1990 | European Pat. Off. . |
| 359537 | 3/1990 | European Pat. Off. . |
| 0377967 | 7/1990 | European Pat. Off. . |
| 0402716 | 12/1990 | European Pat. Off. . |
| 412531 | 2/1991 | European Pat. Off. . |
| 462761 | 12/1991 | European Pat. Off. . |
| 488616 | 6/1992 | European Pat. Off. . |
| 2801187 | 7/1978 | Germany . |
| WO8 707 607 | 12/1987 | WIPO . |
| 89/09217 | 10/1989 | WIPO . |
| 92/05174 | 4/1992 | WIPO . |
| 92/14733 | 9/1992 | WIPO . |

OTHER PUBLICATIONS

Chemical Abstract vol, 113, No. 171,904d, Sekiya et al, 1990, "Benzene-condensed cyclic amine β-amino carboxamides as antitachycardiacs and vasodilators".

A. P. Terent'ev et al., "Optically active isocyanates. III. Synthesis and spectropolarimetric study of optically active N-derivative of urea", *Chemical Abatracts*, vol. 71, 1969, Abstract No. 69992h, p. 250.

Jose Bermudez et al., "5-Hydroxytryptamine (5-HT$_3$) Receptor Antagonists. 2. 1-Indolinecarboxamides", *J.Med. Chem.*, 1990, vol. 33, pp. 1929–1932.

Paul D. Leeson et al., "4-Amido-2-carboxytetrahydroquinolines, Structure-Activity Relationships for Antagonism at the Glycine Site of the NMDA Receptor", *J. Med. Chem*, 1992, vol. 35, pp. 1954–1968.

John L. Hughes et al., "Cardiovascular Activity of Aromatic Guanidine Compounds", *J. Med. Chem.*, 1975, vol. 18, No. 11, pp. 1077–1088.

M. Mazza et al., "N-Acilindoline Ad Attivita Fitotossica", *Farmaco. Ed. Sci.*, vol. 31, No. 10, 1976, pp. 746–754.

H. J. Petersen et al., *J. of Med. Chem.*, vol. 21, No. 8, 1978:773–781, Washington, D.C. (1978).

V. A. Ashwood et al., "Synthesis and Antihypertensive Activity of 4-(Cyclic Amido)-2H-1-benzopyrans", *J. Med. Chem.*, 1986:29:2194–2201. (1986).

C. R. Rasmussen et al., "Improved Procedures of Cycloalkyl-, Arylalkyl-, and Arylthioureas", *Synthesis*, Juen 1988:456–459. (1988).

V. V. Mozolis et al., "Preparation of N-Substituted Thiourea", *Russian Chemical Reviews*, 42(7):1973:587–595. (1973).

J. M. Evans et al., "Synthesis and Antihypertensive Activity of Su,bstituted trans-4-Amino-3,4-dihydro-2, 2-dimethyl-2H-1-benzopyran-3-ols", *J. Med. Chem.*, 1983:26:1582–1589. (1983).

R. W. Lang et al., "Synthesis of Selectivity Trifluoromethylated Pyridine Derivatives as Potential Antihypertensives", *Helvetica Chimica Acta*, 1988:71:596–601. (1988).

(List continued on next page.)

*Primary Examiner*—C. Warren Ivy
*Assistant Examiner*—Raymond Covington
*Attorney, Agent, or Firm*—Theodore R. Furman, Jr.; Ellen K. Park

[57] ABSTRACT

Novel compounds having potassium channel activating activity and useful, for example, as antiischemic agents are disclosed. These compounds have the general formula

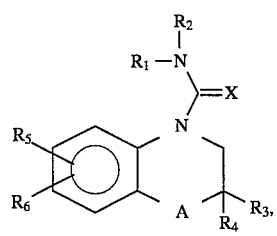

wherein A is

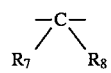

or a single bond to complete an indoline nucleus; X is —O—, —S— or —NCN; and the R groups are as defined herein.

14 Claims, No Drawings

OTHER PUBLICATIONS

P. Sebok et al., "Selective Synthesis of Analogues of the Natural Prococenes Synthesis and Regioselective (–Alkylation of 6–Chloro–and 6–Tert–Butyl–7,8–Dihydroxy–2, 2–Dimethyl–4–Chromanones", *Heterocycles,* 1988:27:2595–2607.

P. Teixidor et al., "Improved Preparation of Precocene II, Unexpected Results in the Reduction of Alkoxy Substituted Acetophenones and 4–Chromanones with Sodium Borohydride", *Heterocycles,* 1988:27:2459–2465.

A. Banerji et al., "Enolats of o–Hydroxyacetophenones: Novel Synthesis of 2,2–Dialkyl–4–Chromanones", *Tetrahedron Let.,* 1979:38:3685–3686.

G. Ariamala et al., "A Simple Route for the Synthesis of 4–Chlorochromenes and Chroman–4–ones", *Tetrahedron Let.,* 1988:vol. 29, No. 28:3487–3488.

R. Albrecht et al., CA77:88182j, (1972), *Abstract of Chim. Ther.,* 1972:7(1):90–13.

AMINOCARBONYL (THIOCARBONYL) AND CYANOGUANIDINE DERIVATIVES OF QUINOLINE AND INDOLINE

This is a Continuation-in-part application of U.S. Ser. No. 07/977,340, Filed Nov. 17, 1992, now abandoned.

SUMMARY OF THE INVENTION

In accordance with the present invention novel compounds having potassium channel activating activity and useful, for example, as antiischemic agents are disclosed. These compounds have the general formula

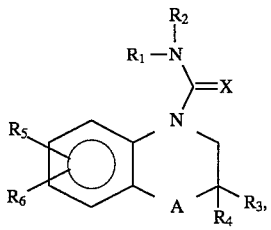

and pharmaceutically acceptable salts thereof wherein

A is

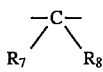

or a single bond to complete an indoline nucleus;

X is —O—, —S— or —NCN;

$R_1$ is aryl, arylalkyl, heterocyclo or (heterocyclo)alkyl;

$R_2$ is hydrogen, alkyl or arylalkyl;

or $R_1$ and $R_2$ taken together form a 5- to 7-membered saturated or unsaturated ring, which may further include an aryl group fused to 2 carbon atoms of such 5- to 7-membered ring;

$R_3$, $R_4$, $R_7$ and $R_8$ are each independently hydrogen, alkyl or arylalkyl; or $R_3$ and $R_4$, or independently $R_7$ and $R_8$, taken together with the carbon atoms to which they are attached form a 5- to 7-membered carbocyclic ring, with the proviso that when A is

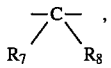

and $R_7$ and $R_8$ are other than hydrogen, then $R_3$ and $R_4$ are hydrogen, or when $R_7$ and $R_8$ are hydrogen then, $R_3$ and $R_4$ are other than hydrogen;

$R_5$ is hydrogen, alkyl, haloalkyl, alkenyl, alkynyl, cycloalkyl, arylalkyl, (cycloalkyl)alkyl, —CN, —NO$_2$, —COR, —COOR, —CONHR, —CON(R)$_2$, —CF$_3$, S-alkyl, —SOalkyl, —SO$_2$alkyl,

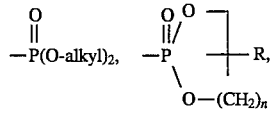

halogen, amino, substituted amino, —O-alkyl, —OCF$_3$, —OCH$_2$CF$_3$, —OCOalkyl, —OCONRalkyl, —NRCOalkyl, NRCOOalkyl or —NRCON(R)$_2$ wherein R is hydrogen, alkyl, aryl, arylalkyl, cycloalkyl, (cycloalkyl)alkyl or haloalkyl;

$R_6$ is hydrogen, alkyl, halo, —OH, amino, substituted amino, —O-alkyl, —OCOalkyl, —OCONRalkyl, —NRCOalkyl, —NRCOOalkyl or —NRCON(R)$_2$; and n is an integer of 1, 2 or 3.

DETAILED DESCRIPTION OF THE PRESENT INVENTION

This invention relates to the novel compounds of formula I which are useful as antiischemic agents.

The term "alkyl" used in defining various symbols refers to straight or branched chain saturated hydrocarbon radicals having up to eight carbons, preferably from one to five carbons. Similarly, the terms "alkoxy" and "alkylthio" refer to such alkyl groups attached to an oxygen or sulfur.

The term "alkenyl" refers to straight or branched chain hydrocarbon radicals having from two to eight carbons and at least one double bond, preferably three to five carbons. The term "alkynyl" refers to straight or branched chain hydrocarbon radicals having from two to eight carbons and at least one triple bond, preferably three to five carbons.

The term "cycloalkyl" refers to saturated carbocyclic rings of 3 to 7 carbon atoms with cyclopropyl, cyclopentyl and cyclohexyl being most preferred.

The term "halo" or "halogen" refers to chlorine, bromine, iodine or fluorine.

The term "halo substituted alkyl" refers to such alkyl groups described above in which one or more hydrogens have been replaced by chloro, bromo, iodo or fluoro groups such as chloromethyl, bromomethyl, trifluoromethyl, pentafluoroethyl, 2,2,2-trichloroethyl or 2,2,2-trifluoroethyl. Trifluoromethyl is preferred.

The term "aryl" refers to phenyl, 1-naphthyl, 2-naphthyl or mono substituted phenyl, 1-naphthyl, 2-naphthyl wherein said substituent is alkyl of 1 to 4 carbons, (amino)alkyl, (substituted amino)alkyl, alkylthio of 1 to 4 carbons, alkoxy of 1 to 4 carbons, halo, nitro, cyano, hydroxy, amino, —NH-alkyl wherein alkyl is of 1 to 4 carbons, —N(alkyl)$_2$ wherein

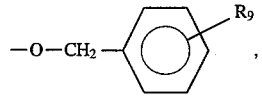

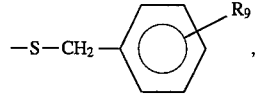

(wherein $R_9$ is hydrogen, alkyl of 1 to 4 carbons, alkoxy of 1 to 4 carbons, alkylthio of 1 to 4 carbons, halo, hydroxy or —CF$_3$), —O—CH$_2$-cycloalkyl, —S—CH$_2$-cycloalkyl, or -alkyl(COOR$_{10}$) (wherein R$_{10}$ is hydrogen or alkyl), and di-substituted phenyl, 1-naphthyl, 2-naphthyl wherein said substituents are methyl, methoxy, methylthio, halo, —CF$_3$, nitro, amino, —OCHF$_2$, or -alkyl(COOR$_{10}$).

Preferred aryl groups include unsubstituted phenyl and monosubstituted phenyl wherein the substituents are nitro, halo, —CF$_3$, alkyl, cyano, methoxy, or -alkyl(COOR$_{10}$).

The term "heterocyclo" refers to fully saturated or unsaturated rings of 5 or 6 atoms containing one or two O and S atoms and/or one to four N atoms provided that the total number of hetero atoms in the ring is 4 or less. The hetero ring is attached by way of an available atom. Preferred monocyclic heterocyclic groups include 2- and 3-thienyl, 2- and 3-furyl, 2-, 3- and 4-pyridyl, and imidazolyl. The term heterocyclo also includes bicyclic rings wherein the five or six membered ring containing O, S and N atoms as defined above is fused to a benzene ring and the bicyclic ring is attached by way of an available carbon atom. Preferred bicyclic hetero groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzodiazolyl, and 4, 5, 6 or 7-benzofuranzanyl.

The term heterocyclo also includes such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino, —NH-alkyl wherein alkyl is of 1 to 4 carbons, —N(alkyl)$_2$ wherein alkyl is of 1 to 4 carbons, —CF$_3$, or —OCHF$_2$; or such monocyclic and bicyclic rings wherein two or three available carbons are substituted with methyl, methoxy, methylthio, halo, —CF$_3$, nitro, hydroxy, amino or —OCHF$_2$.

The term "substituted amino" refers to a group of the formula —NZ$_1$Z$_2$ wherein Z$_1$ is hydrogen, alkyl, cycloalkyl, aryl, arylalkyl, cycloalkylalkyl and Z$_2$ is alkyl, cycloalkyl, aryl, arylalkyl, cycloalkylalkyl or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, or 4-diarylalkyl-1-piperazinyl, each of which may be optionally substituted with alkyl, alkoxy, alkylthio, halo, trifluoromethyl or hydroxy.

The compounds of formula I wherein X is oxygen can be prepared by treatment of a compound of the formula

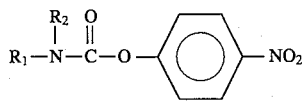

II with a compound of the formula

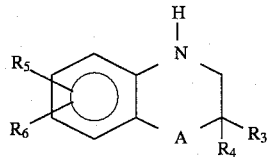

III in an organic solvent, such as dimethylformamide, tetrahydrofuran, acetonitrile or dichloromethane.

Compounds of formula I wherein R$_2$ is hydrogen and X is oxygen or sulfur can also be prepared by reacting a compound of formula III with an isocyanate or isothiocyanate of the formula

R$_1$N=C=X    IV where X is oxygen or sulfur.

Compounds of formula I wherein X is NCN can be prepared by treatment of compounds of formula I wherein X is sulfur with cyanamide in the presence of dicyclohexyl carbodiimide or 1-(3-dimethylaminopropyl)- 2-ethylcarbodiimide hydrochloride.

Compounds of formula I wherein X is NCN can also be prepared by treatment of an intermediate of formula

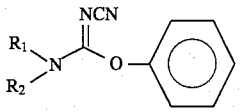

V with a compound of formula III.

Compounds of formula I wherein X is NCN can also be prepared by first treating compounds of formula III with diphenylcyanocarbonimidate in the presence of an organic base such as pyridine or triethylamine, followed by reaction with an amine of formula

VI optionally in the presence of trimethylaluminum.

Compounds of formula II can be prepared, for example, by treatment of a compound of the formula VI with 4-nitrophenylchloroformate.

The compounds of formula III where A is a single bond, R$_5$ is —CN and R$_3$ and R$_4$ are each hydrogen and R$_7$ and R$_8$ are as defined, can be prepared according to Scheme 1.

Scheme 1

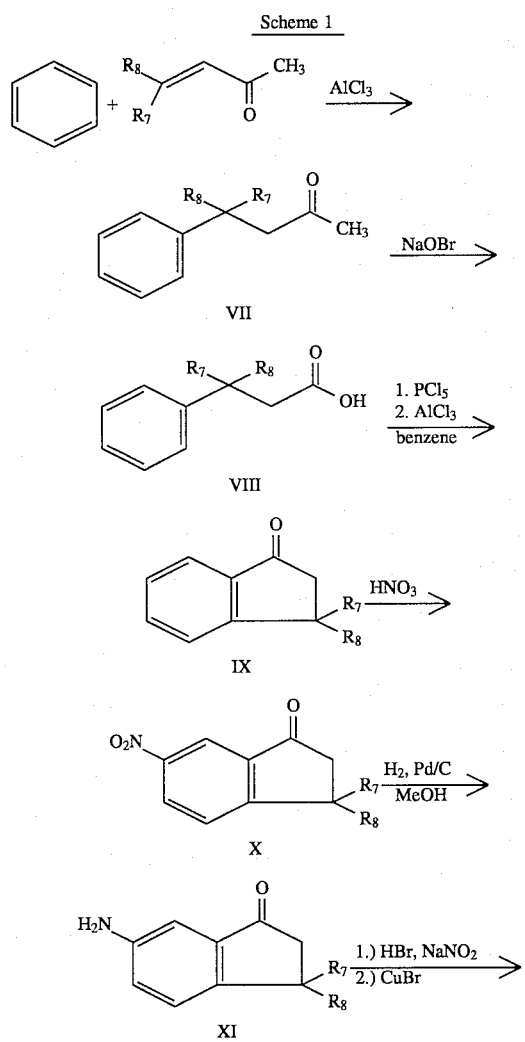

Scheme 1 -continued

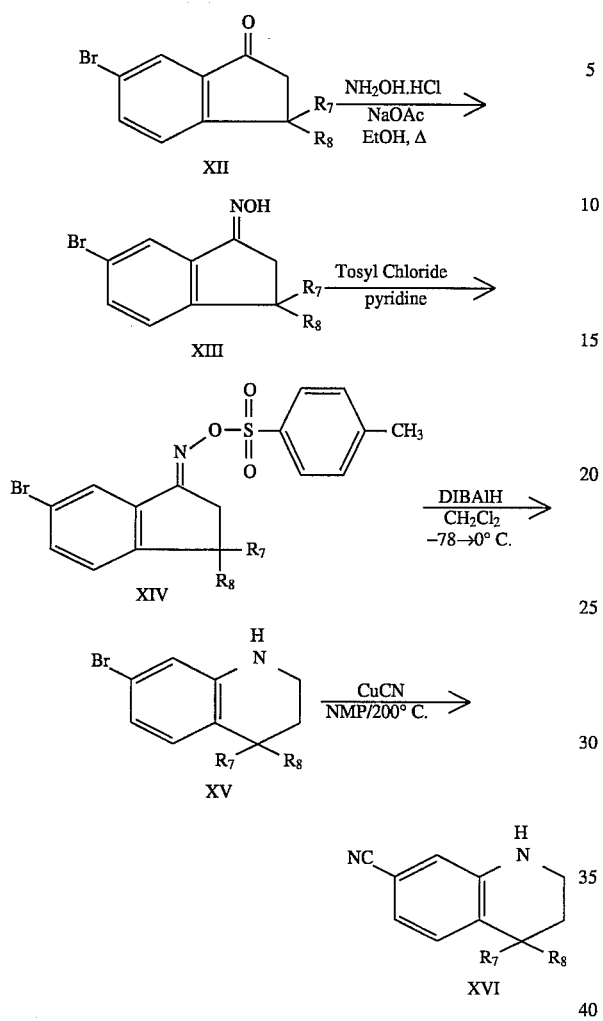

Scheme 2

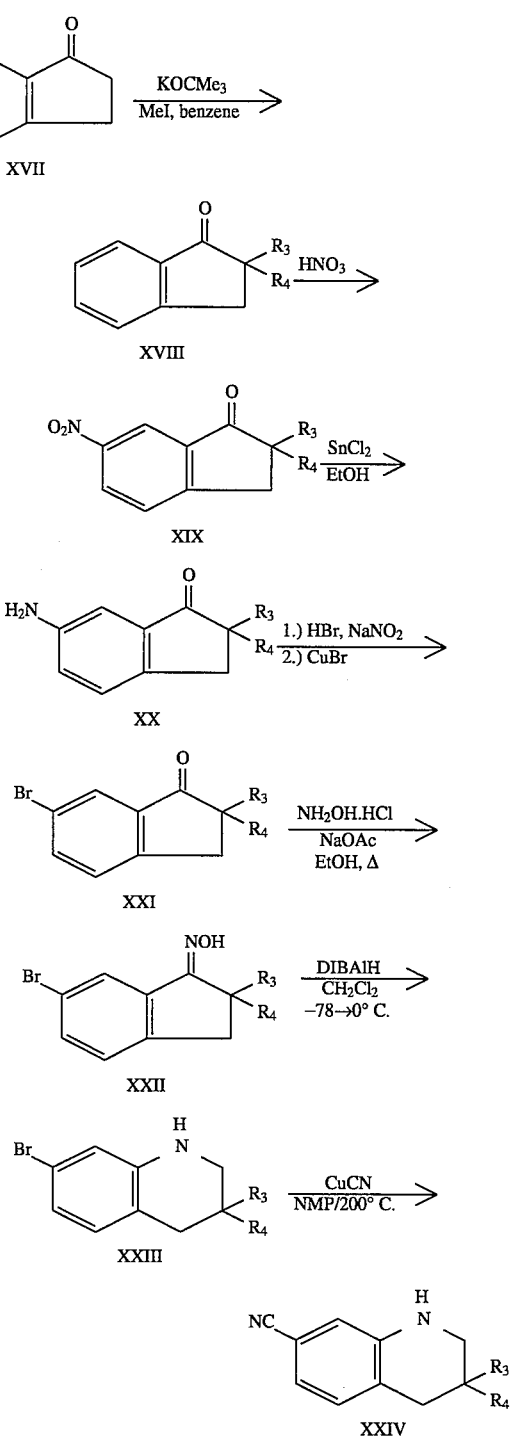

Benzene or a substituted derivative thereof is alkylated with an α,β-unsaturated ketone in the presence of a Lewis acid (aluminum chloride, tin chloride etc.) to provide a compound of formula VII which upon oxidation with, for example sodium hypobromide, gives the acid of formula VIII. The acid is converted to its chloride by treatment with phosphorus oxychloride or thionyl chloride, which on treatment with a Lewis acid gives an indanone of formula IX. The aromatic ring is nitrated with fuming nitric acid to give a compound of formula X which upon catalytic hydrogenation gives the amino compound of formula XI. The amino compound is converted to the bromide XII via its diazonium salt, prepared by treatment with sodium nitrite and hydrobromic acid. The ketone XII is converted to its oxime XIII under standard conditions (hydroxylamine hydrochloride and sodium acetate). The oxime XIII is subjected to reductive Beckman rearrangement (diisobutylaluminum hydride in an organic solvent such as tetrahydrofuran, diethyl ether) via its tosylate XIV, prepared from XIII by treatment with tosyl chloride in the presence of an organic base such as pyridine or triethyl amine. The bromide in the resulting product XV can be replaced with other groups such as nitrile (e.g, XVI), trifluoromethyl, O-alkyl, S-alkyl, alkenyl, alkynyl etc., by methods described in the literature.

Compounds of formula III wherein A is —$CH_2$—, $R_5$ is —CN and $R_3$ and $R_4$ are as defined, can be prepared according to Scheme 2.

The indanone XVII is alkylated with an alkyl halide and a base such as potassium ter-butoxide to give compound XVIII which upon nitration (fuming nitric acid) provides XIX. The nitro group in XIX is changed to the bromide XXI via the same reaction sequence as described for compounds X to XII in Scheme 1. The reductive Beckman rearrangement of oxime XXII proceeded under standard conditions (diisobutylaluminum hydride in tetrahydrofuran) to give bromotetrahydroquinoline XXIII in good overall yield. The bromine in XXIII can be changed to other groups (e.g., CN, CF₃, O-alkyl, S-alkyl etc.) under standard conditions, such as those shown for the preparation of compound XXIV.

Compounds of formula III wherein A is a single bond, R₅ is —CN and R₃ and R₄ are as defined, can be prepared according to Scheme 3.

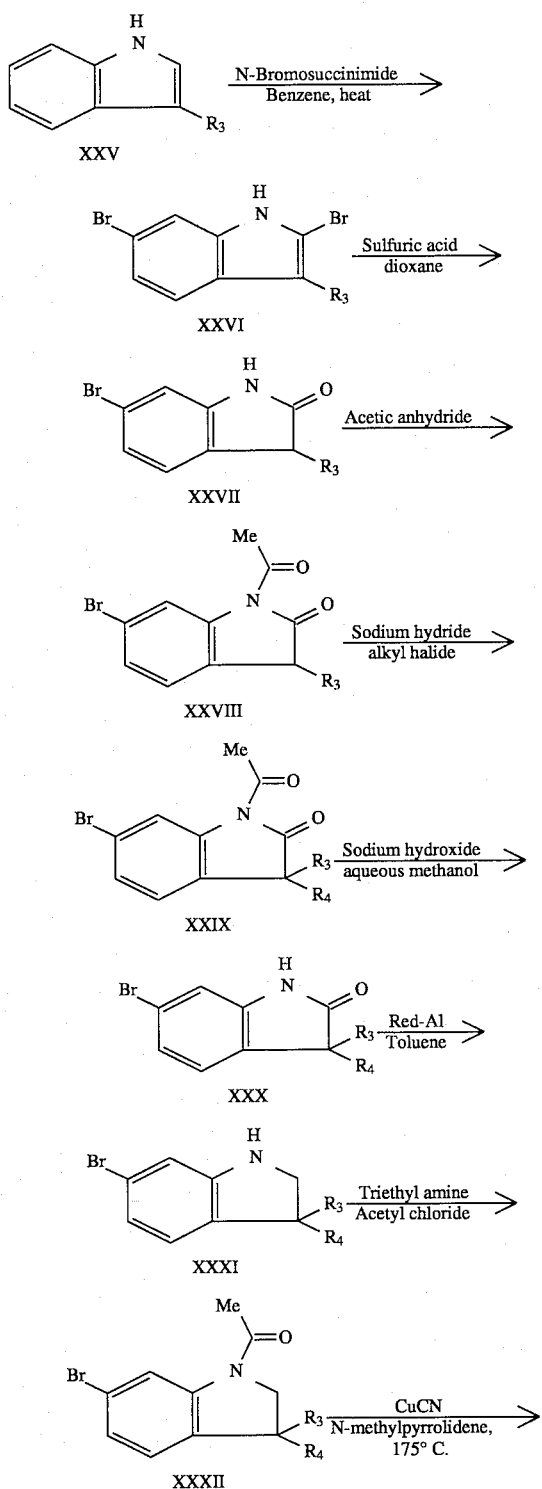

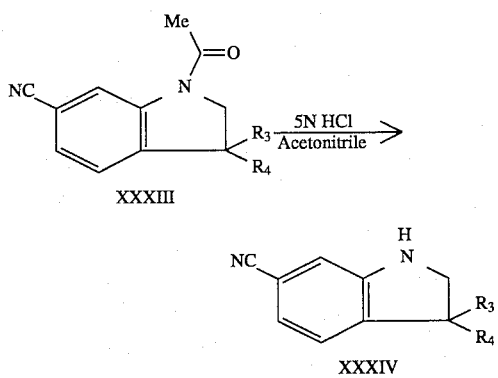

Bromination of indole XXV with N-bromosuccinimide gives the dibromide of formula XXVI which upon acid hydrolysis (sulfuric acid, hydrochloric acid in an organic solvent such as dioxane) provides the amide of formula XXVII. The nitrogen in XXVII is protected (acetic anhydride and an organic base such as pyridine or triethylamine) and the resulting acetamide XXVIII is alkylated with an alkyl halide and a base such as sodium hydride to give XXIX. The acetate in XXIX is removed by treatment with an aqueous base such as sodium hydroxide and the amide XXX is reduced with a reducing agent such as sodium bis(2-methoxyethoxy)aluminum hydride (Red-Al). The resulting product XXXI is protected (acetic anhydride and an organic base such as pyridine or triethyl amine) as an acetamide XXXII and the bromine is changed to an appropriate group (e.g., CN, CF₃, O-alkyl, S-alkyl etc.) under standard conditions. The acetamide protecting group is then removed by treatment with aqueous acid (hydrochloric acid, sulfuric acid in an organic solvent such as dioxane) to provide a compound of formula XXXIV.

Compounds of formula IV are commercially available.

Compounds of the formula V can be prepared by treatment of compounds of the formula VI with diphenylcyanocarbonimidate.

Compounds of formula VI are commercially available.

The compounds of the present invention can have asymmetric centers at carbons 2–4 of tetrahydroquinoline or carbons 2, 3 of indoline rings. Also, any one of the R's can have an asymmetric carbon. Consequently, compounds of formula I can exist in diastereomeric forms or in mixtures thereof. The above described process can utilize racemates, enantiomers or diastereomers as starting materials. When diastereomeric products are prepared, they can be separated by conventional chromatographic or fractional crystallization methods.

The compounds of the present invention wherein R₂ is hydrogen can exist as a mixture of tautomers represented by the following structures. The tautomeric products are obtained in relative amounts that differ from compound to compound. All forms are included in the scope of formula such as compounds of formula

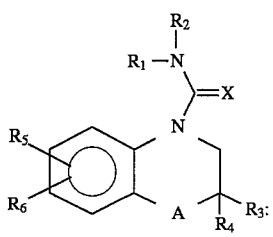

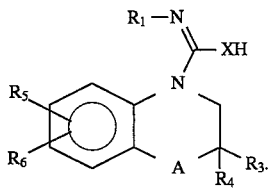

Preferred compounds are those wherein
A is

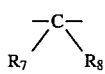

or a single bond;

$R_1$ is aryl, arylalkyl, heterocyclo or (heterocyclo)alkyl;

$R_2$ is hydrogen or alkyl;

$R_3$ and $R_4$ are independently hydrogen or alkyl;

$R_5$ is an electron withdrawing group;

$R_6$ is hydrogen, alkyl or O-alkyl;

$R_7$ and $R_8$ are independently hydrogen or alkyl; and

X is O or NCN.

Most preferred are those compounds wherein
A is

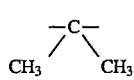

or a single bond;

$R_1$ is phenyl, phenylmethyl, substituted phenyl, substituted phenylmethyl or pyridyl;

$R_2$ is hydrogen;

$R_3$ and $R_4$ are independently hydrogen or methyl;

$R_5$ is —CN or —$NO_2$;

$R_6$ is hydrogen;

$R_7$ and $R_8$ are independently hydrogen or methyl; and

X is O or NCN.

The compounds of formula I and the pharmaceutically acceptable salts act as potassium channel activators. Thus, compounds of the present invention are useful cardiovascular agents, e.g. as antiarrhythmic agents and antiischemic agents.

Compounds of formula I are particularly useful as antiischemic agents since they have been found to possess little or no vasodilatory activity. Thus, compounds of formula I are useful for the treatment of ischemic conditions, e.g. myocardial ischemia, cerebral ischemia, lower limb ischemia and the like. The selectivity, i.e., antiischemic activity with little or no vasodilatory activity, means that in the treatment of, for example, ischemic heart, these compounds are less likely to cause coronary steal, profound hypotension and coronary underperfusion. By little or no vasodilation activity is meant that these compounds have $IC_{50}$ (rat aorta) values greater than that of the potassium channel activator, cromakalim. The "selective" antiischemic agents typically are those having $IC_{50}$ (rat aorta) values >10 times that of cromakalim (i.e., have 1/10 the vasodilatory action) and preferably those having $IC_{50}$ values >50 times that of cromakalim.

Thus, for example, by the administration of a composition containing one (or a combination) of the compounds of this invention, ischemic conditions of a mammalian (e.g., human) host are reduced. A single dose, or preferably two to four divided daily doses, provided on a basis of about 0.00 1 to 100 mg per kilogram of body weight per day, preferably from about 0.1 to about 25 mg per kilogram per day, is appropriate to reduce ischemic conditions. The substance is preferably administered orally, but parenteral routes, such as the subcutaneous, intramuscular, or intravenous routes or any other convenient delivery system, such as inhalation or intranasal solutions or transdermal patches, can also be employed. The above doses are also suitable for the other cardiovascular and non-cardiovascular uses.

As a result of the potassium channel activating activity of compounds of this invention, these compounds are also useful in the treatment of cardiovascular disorders. For example, compounds of the present invention are useful as therapy for congestive heart failure, as anti-anginal agents, as anti-fibrillatory agents, and in limiting myocardial infarction.

Compounds of the present invention are additionally expected to be useful in the treatment of central nervous system disorders (e.g., Parkinsonism, as anti-tremor agents, epilepsy).

The compounds of this invention can also be formulated in combination with a diuretic such as, chlorothiazide, hydrochlorothiazide, flumethiazide, hydroflumethiazide, bendroflumethiazide, methylchlothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Specific embodiments of the present invention are described hereinafter in the following examples.

EXAMPLE 1

7-Cyano-3,4-dihydro-4,4-dimethyl-N-phenyl-1(2H)-quinolinecarboxamide

A. 4-Methyl-4-phenyl-2-pentanone

To a slurry of $AlCl_3$ (40.0 g, 0.3 mole) in benzene (90 mL) maintained at 10° C. under argon was added dropwise mesityl oxide (0.2 mole, 19.63 g). Upon completion of the addition the reaction was stirred at room temperature for 1.5 hours. The reaction mixture was poured onto ice/10% HCl (350 g). The organic layer was separated and the aqueous layer was extracted with ethyl acetate (100 mL). The combined organics were washed with distilled $H_2O$, saturated $NaHCO_3$ solution, saturated NaCl solution and dried over $Na_2SO_4$. The solvent was recovered under vacuum and the crude product (31.6 g) was vacuum distilled (b.p.=107° C. @ 3.0 mmHg) to obtain 24.5 g (69%) of the title A compound as a colorless oil. MS: (M+H)+ @ 177.

B. 3-Methyl-3-phenylbutanoic acid

To a solution of NaOH (47.2 g, 1.18 mole) in ice/$H_2O$ (270 g) maintained at 4°–5° C. was added $Br_2$ (68.7 g, 0.43 mole) followed by 4-methyl-4-phenyl-2-pentanone (23.7 g, 0.135 mole). The reaction was stirred for 18 hours at room temperature. The crude reaction mixture was extracted with $CCl_4$ (discarded), acidified to pH 1–2 with concentrated HCl solution and extracted with ethyl acetate. The combined organics were washed with saturated NaCl solution, dried over $Na_2SO_4$ and evaporated in vacuo to obtain 22.5 g of the title B compound as an off-white solid. This was used in the next step without further purification. MS: $(M+NH_4)+$ @ 196.

C. 3,3-Dimethyl-1-indanone

To a solution of 3-methyl-3-phenyl butanoic acid (17.1 g, 95.5 mmoles) in benzene (70 mL) was added $PCl_5$ (23.0 g, 0.11 mole, 1.15 eq.) portionwise with cooling. Upon completion of the addition, the reaction mixture was refluxed for 30 minutes and cooled to room temperature. Aluminum chloride (13.1 g, 98.3 mmoles) was added in increments and the reaction was heated at reflux for 30 minutes. The reaction mixture was poured onto ice; the oily layer was separated and the aqueous layer was extracted with ethyl acetate. The combined organics were washed with 5% HCl solution, saturated $NaHCO_3$ solution, saturated NaCl solution and dried over $MgSO_4$. The solvent was evaporated in vacuo and the crude product (14.3 g) was vacuum distilled (b.p.=103° C. @ 2.3 mmHg) to obtain 9.98 g of the title C compound as a colorless oil. MS: (M+H)+ @ 161.

D. 1,1-Dimethyl-5-nitro-3-indanone

A mixture of nitric acid (90% fuming, 35 mL) and urea (0.17 g) was cooled to –10° C. and purged with air for 20 minutes; 3,3-dimethyl-1-indanone (8.68 g, 54.2 mmoles) was added and the reaction was stirred for two hours at –10° C. to 5° C. The reaction mixture was poured into ice/$H_2O$ and extracted with ethyl acetate. The combined extracts were washed with distilled $H_2O$, saturated $NaHCO_3$ solution, saturated NaCl solution, and dried over $MgSO_4$. The solvent was recovered under vacuum to obtain 10.0 g of a yellow solid. The crude product was recrystallized from methanol in two crops to obtain 8.08 g (71%) of the title D compound as yellow needles. MS: M– @ 205.

E. 5-Amino-1,1-dimethyl-indan-3-one

A solution of the title D compound (6.5 g, 31,7 mmoles) in methanol (150 mL) containing 5% Pd/C (0.75 g) was stirred under $H_2$ at 15 psi for four hours. The catalyst was filtered and the methanol was recovered under vacuum to obtain 5.72 g of the title E compound as a green solid. The reaction product was used in the next step without further purification.

F. 5-Bromo-1,1-dimethylindan-3-one

To a solution of the title E compound (6.02 g, 34.4 mmole) in a mixture of 48% aqueous HBr solution (9.7 mL) and ethanol (30 mL) cooled to 0° C. was added $NaNO_2$ until a positive starch-iodide test was obtained. The cold diazonium salt solution was added via pipette to a mixture of CuBr (5.42 g, 18.9 mmole) and 48% aqueous HBr solution at 95° C. The reaction mixture was heated at reflux for 15 minutes, cooled to room temperature and partitioned between ethyl acetate and distilled $H_2O$. The organic phase was washed with saturated $NaHCO_3$ solution, saturated NaCl solution, dried over $MgSO_4$ and evaporated in vacuo to obtain 7.33 g of an orange solid. The crude product was chromatographed on silica eluting with hexane/ethyl acetate (4:1) to obtain 6.52 g of the title F compound as a yellow solid; m.p. 117°–118° C.

G. 5-Bromo-1,1-dimethylindan-3-one oxime

A solution of the title F compound (6.52 g, 27.3 mmole) in ethanol (130 mL) containing $NH_2OH.HCl$ (3.79 g, 54.5 mmole) and sodium acetate (4.03 g, 49.1 mmole) was heated at reflux for 2.5 hours. The solvent was recovered under vacuum and the residue was partitioned between ethyl acetate and distilled $H_2O$. The organic phase was washed with saturated NaCl, dried over $MgSO_4$, and evaporated in vacuo to obtain 6.94 g of the title G compound as a yellow solid. The product was used in the next step without further purification; m.p. 115°–117° C.

H. 5-Bromo-1,1-dimethylindan-3-one oxime tosylate

To a solution of the title G compound (5.30 g, 20.9 mmole) in pyridine (50 mL) cooled to 0° C. was added p-toluenesulfonyl chloride (4.77 g, 25.0 mmole). The solution was warmed to room temperature and stirred for 18 hours. The reaction mixture was diluted with ethyl acetate and washed with cold 10% aqueous HCl solution, distilled $H_2O$, saturated $NaHCO_3$ solution, saturated NaCl solution and dried over $MgSO_4$. The solvent was recovered under vacuum to obtain 8.74 g of the title H compound as an orange gum which slowly crystallized on standing. The compound was used in the next step without further purification.

I. 7-Bromo-3,4-dihydro-4,4-dimethyl-1(2H)-quinoline

To a solution of the title H compound (7.74 g, 19.0 mmole) in methylene chloride (95.0 mL) cooled to –78° C. was added diisobutylaluminum hydride (1M solution in hexane, 95.0 mL). The reaction mixture was stirred 0.5 hours at –78° C. followed by five hours at 0° C. The crude product solution was diluted with methylene chloride (200 mL) and quenched while stirring vigorously by the addition of sodium fluoride (16.0 g) and distilled $H_2O$ (5.20 g). The solids were filtered and the filtrate was dried over $MgSO_4$ and evaporated in vacuo to obtain 4.80 g of an orange gum. The crude product was chromatographed on silica eluting with 15% ethyl acetate in hexane to obtain 2.23 g of the title I compound as a light yellow oil.

J.
7-Cyano-3,4-dihydro-4,4-dimethyl-1(2H)-quinoline

A mixture of the title I compound (2.24 g, 9.33 mmole), CuCN (1.67 g, 18.7 mmole) and 1-methyl-2-pyrrolidinone (22.5 mL) was heated at 185°–190° C. for 3.25 hours. The reaction mixture was diluted with ethyl acetate and filtered. The volatiles were recovered under vacuum and the residue was chromatographed on silica eluting with 15% ethyl acetate in hexane to obtain 0.92 g (53%) of the desired title J product as a light yellow oil.

K.
7-Cyano-3,4-dihydro-4,4-dimethyl-N-phenyl-1(2H)-quinolinecarboxamide

A solution of the title J compound (0.20 g, 1.07 mmole), phenyl isocyanate (0.13 g, 1.07 mmole) and 4-dimethylaminopyridine (50 mg) in acetonitrile (4.5 mL) was heated under argon at reflux for one hour. The solvent was recovered under vacuum and the residue was triturated with isopropyl ether to afford 0.27 g of the title compound as an off-white solid; m.p. 174–175C.

Analysis calculated for $C_{19}H_{19}N_3O$: C, 74.73; H, 6.27; N, 13.76; Found: C, 74.46; H, 6.26; N, 13.77.

EXAMPLE 2

7-Cyano-3,4-dihydro-4,4-dimethyl-N-(phenylmethyl)-1(2H)-quinolinecarboxamide

A solution of the title J compound from Example 1 (0.20 g, 1.07 mmole), benzyl isocyanate (0.14 g, 1.07 mmole) and 4-dimethylaminopyridine (50 mg) in acetonitrile (4.5 mL) was heated under argon at reflux for one hour. The solvent was recovered under vacuum and the crude product was chromatographed on silica eluting with hexane/ethyl acetate (7:3) to afford 0.30 g of the title compound as a white solid; m.p. 114°–115° C.

Analysis calculated for $C_{20}H_{21}N_3O$: C, 75.21; H, 6.63; N, 13.16; Found: C, 75.05; H, 6.63; N, 12.98.

EXAMPLE 3

N-(3-chlorophenyl)-7-cyano-3,4-dihydro-4,4-dimethyl-1-(2H)-quinolinecarboxamide

A solution of 7-cyano-3,4-dihydro-4,4-dimethyl-1(2H)-quinoline (0.16 g, 0.86 mmoles, compound of example 1, part J) and 3-chlorophenyl-isocyanate (0.14 g, 0.90 mmoles) in acetonitrile (3.75 mL) containing N,N-dimethylaminopyridine (30 mg) was heated at reflux under argon for three hours. The solvent was recovered under vacuum to obtain 0.38 g of crude product as a yellow gum. The crude material was purified by chromatography on silica eluting with hexane/ethyl acetate (3:1) to obtain 270 mg of a white solid. The chromatography isolate was further purified by crystallization from isopropanol to obtain the title compound (190 mg, 65%) as a white solid; m.p. 150°–152° C. MS:(M+H)+ @ 340.

Analysis calculated for $C_{19}H_{18}ClN_3O \cdot 0.22\ H_2O$: C, 66.38; H, 5.41; N, 12.22; Cl, 10.31; Found: C, 66.55; H, 5.37; N, 12.05; Cl, 10.50.

EXAMPLE 4

7-Cyano-1,2,3,4-tetrahydro-3,3-dimethyl-N-phenyl-1-quinolineamide

A. 3,3-Dimethylindan-1-one

To a solution of 1-indanone (30 g, 0.23 mole) in dry benzene (350 mL) at room temperature under argon was added solid potassium-(ter)-butoxide (95%, 68 g, 0.58 mole). Methyl iodide (65.3 g, 0.46 mole) was added to the deep purple slurry with cooling over one hour. The reaction mixture was heated at reflux for two hours and poured over 400 g of ice containing concentrated HCl solution (90 mL). Diethyl ether was added and the organic phase was separated. The aqueous phase was extracted with diethyl ether. The combined organic layers were washed with 5% sodium carbonate solution followed by saturated sodium chloride solution. The extracts were dried over magnesium sulfate and evaporated in vacuo to obtain 40 g of a dark brown oil. The oil was dissolved in ethyl acetate, treated with activated charcoal, and filtered through a pad of celite and silica gel. The filtrate was concentrated to obtain 34.6 g of an orange solid. The partially purified material was triturated with cold pentane to afford 24.3 g (66%) of the title compound as a yellow solid. MS: (M+H)+ @ 161.

B. 3,3-Dimethyl-6-nitroindan-1-one

A solution of urea (0.40 g) in nitric acid (90% fuming, 80 mL) was purged with air for twenty minutes, then cooled to −5° C. To this solution was added the title A compound (20.0 g, 0.12 mole) in portions while maintaining the reaction temperature <5° C. The reaction mixture was stirred at −5° to +5° C. for two hours and poured over ice. The aqueous mixture was extracted with ethyl acetate. The extracts were washed with saturated sodium bicarbonate solution, saturated sodium chloride solution, and dried over magnesium sulfate. The solvent was recovered under vacuum to obtain 27.3 g of an orange solid. The crude material was crystallized from methanol to obtain 18.0 g (73%) of the title compound as a yellow crystalline solid. MS: (M+NH4)+ @ 223.

C. 6-Amino-3,3-dimethylindan-1-one

To a solution of the title B compound (10.0 g, 48.7 mmole) in ethanol (100 mL) was added stannous chloride dihydrate (54.9 g, 0.24 mole). The mixture was heated at 75° C. for one hour. The reaction mixture was poured over ice and neutralized by the addition of solid sodium bicarbonate. The pH was adjusted to 11–12 with 10N sodium hydroxide solution and the reaction mass was extracted with ethyl acetate. The extracts were washed with saturated sodium chloride solution, dried over magnesium sulfate and evaporated in vacuo to obtain 8.19 g (96%) of the title compound as a tan solid. The compound was used in the next step without further purification.

D. 6-Bromo-3,3-dimethylindan-1-one

To a solution of title C compound (21.48 g, 71.2 mmole) in ethanol (65 mL) cooled to 0° C. was added 48% aqueous HBr (20 mL) followed by sodium nitrite solution (4.91 g dissolved in 8.8 mL of $H_2O$) until a positive starch/iodide test result was obtained. The cold diazonium salt solution was added directly via pipette to a refluxing mixture of CuBr (11.23 g, 78.3 mmole) and 48% aqueous HBr (20 mL). The reaction mixture was refluxed an additional 15 minutes upon completion of the addition, cooled to room temperature, and partitioned between ethyl acetate and 2N HCl. The organic phase was washed with 2N HCl, sainted sodium bicarbonate solution, saturated sodium chloride solution, and dried over magnesium sulfate. The solvent was recovered under vacuum to obtain 15.55 g of an orange solid. The product was purified by trituration with cold pentane to obtain 13.17 g (77%) of the title compound as a pale yellow solid. MS: (M+H)+ @ 239.

E. 6-Bromo-3,3-dimethylindan-1-one oxime

A mixture of title D compound (11.64 g, 48.67 mmole), hydroxylamine hydrochloride (6.76 g, 97.3 mmole) and sodium acetate (7.19 g, 87.6 mmoles) in ethanol (230 l) was heated at reflux for 36 hours. The ethanol was recovered under vacuum and the residue was partitioned between distilled $H_2O$ and ethyl acetate. The organic fraction was washed with 1N NaOH solution, saturated sodium chloride solution, dried over magnesium sulfate and evaporated in vacuo to obtain 12.27 g (99%) of an off-white solid as a 2.9:1 mixture of syn and anti oximes. The isomer mixture was chromatographed on silica eluting with 7.5% ethyl acetate in hexane to afford 8.94 g of the title product (syn isomer) as a white solid. MS: (M+H)+ @ 254.

F.
7-Bromo-3,3-dimethyl-1,2,3,4-tetrahydro-1-quinoline

To a solution of title E compound (5.0 g, 19.7 mmole) in methylene chloride (200 mL) at 0° C. was added diisobutylaluminum hydride solution (1M in hexane, 5 eq., 147 mL) dropwise with stirring. The reaction mixture was stirred at 0° C. for 18 hours after which time it was diluted with methylene chloride (400 mL) and quenched by the addition of sodium fluoride (24.8 g) followed by distilled $H_2O$ (8 mL). The solids were filtered and the filtrate was evaporated under vacuum to obtain an off-white solid (5.0 g). The crude material was chromatographed on silica eluting with hexane/ethyl acetate (9:1 ) to obtain the title compound (2.26 g, 48%) as a white solid.

G.
7-Cyano-3,3-dimethyl-1,2,3,4-tetrahydro-quinoline

A solution of title F compound (3.75 g, 15.6 mmole) in 1-methyl- 2-pyrrolidinone (40 mL) containing copper(I)cyanide (2.80 g, 31.2 mmole) was heated at 180° C. for two hours. The reaction mixture was cooled to room temperature, diluted with a large volume of diethyl ether, and filtered. The filtrate was washed with 1N sodium hydroxide solution followed by saturated sodium chloride solution and dried over sodium sulfate. The solvent was evaporated in vacuo to obtain 2.89 g of a brown solid. The crude product was chromatographed on silica eluting with 15% ethyl acetate in hexane to obtain the title G product (1.80 g, 62%) as a yellow solid. MS: (M+H)+ @ 187.

H.
7-cyano-1,2,3,4-tetrahydro-3,3-dimethyl-N-phenyl-1-quinolinamide

A solution of title G compound (0.275 g, 1.48 mmoles) and phenylisocyanate (0.18 g, 1.49 mmoles) in acetonitrile (6 mL) containing a catalytic amount of N,N-dimethylaminopyridine was heated at reflux under argon for one hour. The solvent was evaporated in vacuo and the residue thus obtained was triturated with isopropyl ether to afford the title compound 0.44 g (97%) as a colorless solid; m.p. 170°–171° C. MS: (M+H)+ @ 306.

Analysis calculated for $C_{19}H_{19}N_3O$: C, 74.73; H, 6.27; N, 13.76; Found: C, 74.62; H, 6.22; N, 13.74.

EXAMPLE 5

7-Cyano-1,2,3,4-tetrahydro-3,3-dimethyl-N-(phenylmethyl)-1-quinolineamide

A solution of 7-cyano-1,2,3,4-tetrahydro-3,3-dimethylquinoline (0.30 g, 1.61 mmoles, compound of example 1, part G) and benzylisocyanate (0.18 g, 1.49 mmoles) in acetonitrile (6.75 mL) containing a catalytic amount of N,N-dimethylaminopyridine was heated at reflux under argon for twelve hours. The solvent was evaporated in vacuo and the residue was triturated with isopropyl ether to afford the title compound (0.37 g, 72%) as a colorless solid; m.p. 162°–163° C. MS: (M+H)+ @ 320.

Analysis calculated for $C_{20}H_{21}N_3O.0.12H_2O$: C, 74.71; H, 6.66; N, 13.07; Found: C, 74.80; H, 6.58; N, 12.98.

EXAMPLE 6

7-Cyano-1,2,3,4-tetrahydro-4,4-dimethyl-N-(3-pyridinyl)-1-quinolinecarboxamide

The title compound was prepared from 7-cyano-3,4-dihydro-4,4-dimethyl- 1(2H)-quinoline (compound of example 1, part J) and 3-pyridylisocyanate by the same method as described in example 1, part K. The product was obtained as a colorless powder; m.p. 183°–185° C.

Analysis calculated for $C_{18}H_{18}N_4O.0.1$ethyl acetate.$0.19H_2O$: C, 69.37; H, 6.07; N, 17.59; Found: C, 69.35; H, 5.94; N, 17.32.

EXAMPLE 7

7-Cyano-1,2,3,4-tetrahydro-3,3-dimethyl-N-(3-pyridinyl)-1-quinolinamide

A solution of title 4G compound (0.25 g, 1.34 mmoles) and nicotinyl azide (0.25 g, 1.69 mmoles, precursor for 3-pyridylisocyanate) in toluene (5.0 mL) was heated at 85° C. under argon for three hours. The reaction mixture was partitioned between ethyl acetate and saturated sodium bicarbonate solution. The organic phase was washed with saturated sodium chloride solution, dried over magnesium sulfate and evaporated in vacuo to obtain a colorless foam (0.52 g). The crude product was chromatographed on silica eluting with ethyl acetate to obtain the title compound as a white solid (0.40 g, 97%); m.p. 164°–166° C.

Analysis calculated for $C_{18}H_{18}N_4O.0.23H_2O$: C, 69.63; H, 5.99; N, 18.05; Found: C, 69.99; H, 5.86; N, 17.69.

EXAMPLE 8

6-Cyano-2,3-dihydro-3,3-dimethyl-N-(3-pyridinyl-1H-indole-1-carboxamide

A. 2,6-Dibromo-3-methylindole

A solution of 3-methylindole (13.3 g, 0.1 mole) and N-bromophthalimide (48.2 g, 0.2 mole) in benzene (265 mL) was heated at reflux for one-half hour. The reaction mixture was diluted with ethyl acetate and extracted with 1N sodium hydroxide solution. The organic phase was washed with saturated sodium chloride solution, dried over magnesium sulfate and evaporated in vacuo to obtain a black solid (22 g). The crude material was chromatographed on silica eluting with 5% ethyl acetate in hexane to obtain a tan solid (18.5 g) which was crystallized from hexanes to obtain the title compound as an off-white crystalline solid (14.84 g, 51%).

B. 6-Bromo-3-methyl-2-oxo-indole

A solution of title A compound (12.65 g, 44 mmoles) in dioxane (peroxide free, 250 mL) and 2.5N sulfuric acid (250 mL) was heated at reflux under argon for 24 hours. The reaction mixture was cooled to room temperature, diluted with 1 liter of distilled water and extracted with ethyl acetate. The organic fraction was washed with saturated sodium carbonate solution, saturated sodium chloride solution and dried over magnesium sulfate. The solvent was evaporated in vacuo to give the title compound (9.74 g, 98%) as a yellow solid which was used in the next step without further purification.

C. 6-Bromo-3-methyl-2-oxo-1H-indole-1-acetamide

A solution of title B compound (9.31 g, 41.2 mmoles) in xylene (100 mL) containing acetic anhydride (6.31 g, 1.5 eq.) was heated at reflux for five hours after which time the reaction was incomplete. An additional 0.75 equivalents of acetic anhydride was added and the reaction mixture was heated an additional two hours at reflux. The reaction mixture was cooled to room temperature and diluted with ethyl acetate. The crude product solution was washed with distilled water followed by saturated sodium bicarbonate solution and saturated sodium chloride solution. The solvent extract was dried over magnesium sulfate and the solvent was recovered under vacuum to obtain an orange solid (11.4 g). The crude material was chromatographed on silica eluting with hexane/ethyl acetate (3:1) to obtain the title compound (9.18 g, 78% ) as an off-white solid; m.p.102°–104° C.

Analysis calculated for $C_{11}H_{10}NBrO_2$: C, 49.28; H, 3.76; N, 5.22; Found: C, 49.23; H, 3.74; N, 5.21.

D. 6-Bromo-3,3-dimethyl-2-oxo-1H-indole-1-acetamide

To a solution of title C compound (8.98 g, 33.5 mmoles) in dry tetrahydrofuran (90 mL) under argon and cooled to 0° C. was added sodium hydride dispersion (60% in mineral oil, 1.05 eq., 1.41 g). The reaction mixture became viscous and was diluted with dry tetrahydrofuran (25 mL). After stirring for 10 minutes, methyl iodide (1.05 eq, 4.75 g) was added dropwise. The reaction mixture was stirred two hours at room temperature, quenched by the addition of saturated ammonium chloride solution and extracted with ethyl acetate. The organic phase was washed with distilled water, saturated sodium chloride solution and dried over magnesium sulfate. The solvent was recovered under vacuum to obtain the title compound (9.67 g, 100%) as an off-white solid. $(M+H)^+$ @ 282.

E. 6-Bromo-3,3-dimethyl-2-oxo-indole

A solution of title D compound (9.61 g, 34.1 mmole) in ethanol (80 mL) and 1N sodium hydroxide (20 mL) was stirred at room temperature for one hour. The reaction mixture was partitioned between distilled water and diethyl ether. The organic phase was washed with distilled water, saturated sodium chloride solution and dried over magnesium sulfate. The solvent was recovered under vacuum to obtain the title compound (8.03 g, 98%) as an off-white solid.

F. 6-Bromo-3,3-dimethyl-dihydroindole

To a solution of title E compound (8.0 g, 33.3 mmole) in dry toluene (185 mL) heated to 85° C. was added sodium bis(2-methoxyethoxy)aluminum hydride, (3.4M in toluene, 14.7 mL, 50 mmole) over the course of 15 minutes. The reaction mixture was heated an additional 15 minutes at 85° C., cooled to 0° C. and quenched by the addition of 1N sodium hydroxide solution. The phases were separated and the organic phase was washed with 1N sodium hydroxide solution followed by saturated sodium chloride solution. The product solution was dried over magnesium sulfate and evaporated in vacuo to obtain a tan solid (7.34 g). The crude material was chromatographed on silica eluting with hexane/ethyl acetate (9:1) to obtain the title compound (5.48 g, 73%) as a pale green solid; m.p. 100°–102° C.

Analysis calculated for $C_{10}H_{12}NBr$: C, 53.12; H, 5.35; N, 6.19; Found: C, 53.15; H, 5.32; N, 6.20. MS: $(M+H)^+$ @ 226.

G. 6-Bromo-3,3-dimethyl-1H-indole-1-acetamide

To a solution of title F compound (5.45 g, 24.1 mmole) in methylene chloride (55 mL) containing triethylamine (2.68 g, 26.5 mmol) cooled to 0° C. was added acetyl chloride dropwise over five minutes. The reaction mixture was stirred 45 minutes at room temperature and partitioned between 1N aqueous hydrochloric acid solution and ethyl acetate. The organic phase was washed with saturated sodium bicarbonate solution, saturated sodium chloride solution; dried over magnesium sulfate and evaporated in vacuo to obtain the title compound (6.42 g, 99%) as a pale yellow solid. MS: $(M+H)^+$ @ 268.

H. 6-Cyano-3,3-dimethyl-1H-indole-1-acetamide

A solution of title G compound (6.56 g, 24.5 mmole) in N-methylpyrrolidone (70 mL) containing copper(1)cyanide (4.38 g, 48.9 mmole) was heated under argon at 175° C. for three hours. The reaction mixture was cooled to room temperature, diluted with diethyl ether and filtered. The filtrate was washed with distilled water, 1N aqueous hydrochloric acid solution, saturated sodium bicarbonate solution and saturated sodium chloride solution. The crude product solution was dried over magnesium sulfate and evaporated in vacuo to obtain the title compound (4.37 g, 83%) as an off-white solid. MS: $(M+H)^+$ @ 215.

I. 6-Cyano-3,3-dimethy-dihydrolindole

A solution of title H compound (4.33 g, 20.2 mmole) in a mixture of acetonitrile (120 mL) and 5N aqueous hydrochloric acid (40 mL) was heated at reflux for 1.5 hours. The reaction mixture was cooled to room temperature and carefully neutralized with saturated sodium chloride solution. The oily layer was separated and the aqueous layer was extracted with ethyl acetate. The combined organic layers were washed with saturated sodium chloride solution, dried over sodium sulfate and evaporated in vacuo to obtain a brown oil. The crude material was purified by chromatography on silica gel eluting with hexane/ethyl acetate (3:2) to give the title compound (3.16 g, 91%) as a yellow solid. MS: $(M+H)^+$ @ 173.

J. 6-Cyano-2,3-dihydro-3,3-dimethyl-N-(3-pyridinyl)-1H-indole-1-carboxamide

A solution of title I compound (0.30 g, 1.74 mmoles) and nicotinyl azide (0.32 g, 2.18 mmoles) in toluene (6 mL) was heated at 85° C. for one hour. The reaction mixture was cooled to room temperature and partitioned between ethyl acetate and distilled water. The organic phase was washed with saturated sodium bicarbonate solution followed by saturated sodium chloride solution. The crude product solution was dried over magnesium sulfate and evaporated under vacuum to obtain a yellow solid. The crude material was purified by chromatography on silica gel eluting with 100% ethyl acetate to afford the title compound (0.41 g) as a white solid; m.p. 220°–222° C.

Analysis calculated for $C_{17}H_{16}N_4O$: C, 69.85; H, 5.52; N, 19.16; Found: C, 69.88; H, 5.55; N, 19.00.

EXAMPLE 9

1-[(Cyanoimino)(phenylamino)methyl]-2,3-dihydro-3,3-di-methyl-1H-carbonitrile

A.
1-[(Cyanoimino)(phenoxymethyl)]-2,3-dihydro-3,3-dimethyl-1H-indole- 6-carbonitrile A solution of title title 8I compound (0.65 g, 3.77 mmole), diphenylcyanocarbonimidate (1.08 g, 4.53 mmole) and 1,8-diazabicyclo-[ 5.4.0]undec-7-ene (0.63 g, 4.15 mmole) in 1,2-dichloroethane (26 mL) was heated at reflux under argon for eight hours. The reaction mixture was diluted with ethyl acetate and washed with 2N hydrochloric acid solution, 1N sodium hydroxide solution and saturated sodium chloride solution. The extract was dried over magnesium sulfate and evaporated in vacuo to obtain a yellow solid (1.25 g). The crude material was redissolved in ethyl acetate and filtered through a pad of silica gel to obtain the title compound as a yellow solid (0.99 g, 83%); m.p. 168°–170° C. MS: $(M+H)^+$ @ 317.

B.
1-[(Cyanoimino)(phenylamino)methyl]-2,3-dihydro-3,3-di-methyl-1H-indole- 6-carbonitrile Trimethylaluminum (2M solution in hexane, 1.74 mmole, 0.87 mL) was added to a solution of aniline (0.16 g, 1.74 mmole) in 1,2-dichloroethane (3.25 mL) under argon. The mixture was stirred at room temperature for ½ hour. To the reaction mixture was added a solution of title A compound (0.5 g, 1.58 mmole) in 1,2-dichloroethane (3.25 mL). The reaction mixture was stirred at room temperature for 18 hours, quenched with water, and partitioned between ethyl acetate and 1N sodium hydroxide solution. The organic phase was washed with brine, dried over magnesium sulfate and evaporated in vacuo to obtain a pale yellow solid. This was purified by chromatography on silica gel eluting with ethyl acetate/hexane (1:1) and crystallized from isopropanol to obtain the title product (0.22 g, 44%) as an off-white solid; m.p. 224°–225° C.

Analysis calculated for $C_{19}H_{17}N_5 \cdot 0.30 C_3H_8O$: C, 71.69; H, 5.87; N, 21.01; Found: C, 71.35; H, 5.40; N, 20.80.

What is claimed is:
1. A compound of the formula

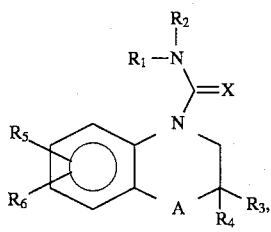

or pharmaceutically acceptable salts thereof wherein
A is

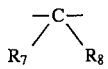

or a single bond to complete an indoline nucleus;
X is —O—, —S— or —NCN;
$R_1$ is aryl, arylalkyl, heterocyclo or (heterocyclo)alkyl;
$R_2$ is hydrogen, alkyl or arylalkyl;
or $R_1$ and $R_2$ taken together form a 5- to 7-membered saturated or unsaturated ring, which may further include an aryl group fused to 2 carbon atoms of such 5- to 7-membered ring;
$R_3$, $R_4$, $R_7$ and $R_8$ are each independently hydrogen, alkyl or arylalkyl; or $R_3$ and $R_4$, or independently $R_7$ and $R_8$ taken together with the carbon atoms to which they are attached form a 5- to 7-membered carbocyclic ring, with the proviso that when A is

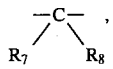

and $R_7$ and $R_8$ are other than hydrogen, then $R_3$ and $R_4$ are hydrogen, or when $R_7$ and $R_8$ are hydrogen then, $R_3$ and $R_4$ are other than hydrogen;
$R_5$ is hydrogen, alkyl, haloalkyl, alkenyl, alkynyl, cycloalkyl, arylalkyl, (cycloalkyl)alkyl, —CN, —NO$_2$, —COR, —COOR, —CONHR, —CON(R)$_2$, —CF$_3$, —S-alkyl, —SOalkyl, —SO$_2$alkyl,

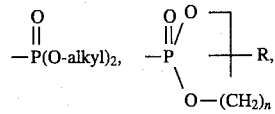

halogen, amino, substituted amino, —O-alkyl, —OCF$_3$, —OCH$_2$CF$_3$, —OCOalkyl, —OCONRalkyl, —NRCOalkyl, —NRCOOalkyl or —NRCON(R)$_2$ wherein R is hydrogen, alkyl, aryl, arylalkyl, cycloalkyl, (cycloalkyl)alkyl or haloalkyl;
$R_6$ is hydrogen, alkyl, halo, —OH, amino, substituted amino, —O-alkyl, —OCOalkyl, —OCONRalkyl, —NRCOalkyl, —NRCOOalkyl or —NRCON(R)$_2$; and n is an integer of 1, 2 or 3; with the proviso that when A is a single bond and $R_1$ is aryl, then $R_3$ and $R_4$ are both alkyl.
2. A compound of claim 1 wherein
A is

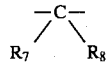

or a single bond, $R_1$ is aryl, arylalkyl, heterocyclo or (heterocyclo)alkyl;
$R_2$ is hydrogen or alkyl;
$R_3$ and $R_4$ are independently hydrogen or alkyl;
$R_5$ is an electron withdrawing group;
$R_6$ is hydrogen, alkyl or O-alkyl;
$R_7$ and $R_8$ are independently hydrogen or alkyl; and
X is O or NCN.

3. A compound of claim 1 wherein
A is

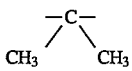

or a single bond, $R_1$ is phenyl, phenylmethyl, substituted phenyl, substituted phenylmethyl or pyridyl;
$R_2$ is hydrogen;
$R_3$ and $R_4$ are independently hydrogen or methyl;
$R_5$ is —CN or —$NO_2$;
$R_6$ is hydrogen;
$R_7$ and $R_8$ are independently hydrogen or methyl; and
X is O or NCN.

4. A compound of claim 1 which is 7-cyano-3,4-dihydro-4,4-dimethyl-N-phenyl- 1(2H)-quinoline-carboxamide.

5. A compound of claim 1 which is 7-cyano-3,4-dihydro-4,4-dimethyl-N-(phenylmethyl)- 1(2H)-quinoline-carboxamide.

6. A compound of claim 1 which is N-(3-chlorophenyl)-7-cyano-3,4-dihydro- 4,4-dimethyl-1-(2H)-quinoline-carboxamide.

7. A compound of claim 1 which is 7-cyano-1,2,3,4-tetrahydro-3,3-dimethyl-N-phenyl- 1-quinoline-amide.

8. A compound of claim 1 which is 7-cyano-1,2,3,4-tetrahydro-3,3-dimethyl-N-(phenylmethyl)- 1-quinoline-amide.

9. A compound of claim 1 which is 7-cyano-1,2,3,4-tetrahydro-4,4-dimethyl-N-( 3-pyridinyl)-1-quinoline-carboxamide.

10. A compound of claim 1 which is 7-cyano-1,2,3,4-tetrahydro-3,3-dimethyl-N-( 3-pyridinyl)-1-quinolinamide.

11. A compound of claim 1 which is 6-cyano-2,3-dihydro-3,3-dimethyl-N-( 3-pyridinyl)-1H-indole-1-carboxamide.

12. A compound of claim 1 which is 1-[(cyanoimino)(phenylamino)methyl]- 2,3-dihydro-3,3-di-methyl-1H-carbonitrile.

13. A pharmaceutical composition comprising an effective amount of a compound of claim 1 and a pharmaceutically acceptable carrier therefor.

14. A method of treating an ischemic condition in a mammalian specie comprising administering to a mammal in need thereof an effective amount of a compound of claim 1.

* * * * *